United States Patent
Wu et al.

(10) Patent No.: US 10,735,648 B2
(45) Date of Patent: Aug. 4, 2020

(54) IMAGING SYSTEM AND IMAGING METHOD

(71) Applicant: QISDA CORPORATION, Taoyuan (TW)

(72) Inventors: Chuang-Wei Wu, Taipei (TW); Min-Hsiung Huang, New Taipei (TW); Chen-Cheng Chiang, Taipei (TW); Tsung-Hsi Lee, Tainan (TW)

(73) Assignee: Qisda Corporation, Taoyuan (TW)

( * ) Notice: Subject to any disclaimer, the term of this patent is extended or adjusted under 35 U.S.C. 154(b) by 0 days.

(21) Appl. No.: 16/299,156

(22) Filed: Mar. 12, 2019

(65) Prior Publication Data

US 2020/0204728 A1    Jun. 25, 2020

(30) Foreign Application Priority Data

Dec. 25, 2018    (CN) .......................... 2018 1 1586902

(51) Int. Cl.
| | |
|---|---|
| *G01B 11/25* | (2006.01) |
| *G06T 19/20* | (2011.01) |
| *H04N 5/232* | (2006.01) |
| *G06T 19/00* | (2011.01) |
| *G06K 9/00* | (2006.01) |

(52) U.S. Cl.
CPC ....... *H04N 5/23229* (2013.01); *G01B 11/254* (2013.01); *G06K 9/00214* (2013.01); *G06T 19/003* (2013.01); *G06T 19/20* (2013.01)

(58) Field of Classification Search
CPC ................................................. H04N 5/23229; G01B 11/254; G06T 19/003; G06T 19/20; G06K 9/00214
See application file for complete search history.

(56) References Cited

U.S. PATENT DOCUMENTS

| | | | | |
|---|---|---|---|---|
| 2007/0052811 | A1* | 3/2007 | Suzuki ................... | H04N 5/232 348/222.1 |
| 2014/0267883 | A1* | 9/2014 | Vidal-Naquet ........... | G06T 7/00 348/362 |
| 2014/0355682 | A1* | 12/2014 | Piroddi ................... | G06T 7/254 375/240.14 |
| 2015/0077590 | A1* | 3/2015 | Kuriyama ............ | H04N 5/2353 348/231.99 |
| 2016/0344952 | A1* | 11/2016 | Ichihara ............... | H04N 13/232 |
| 2016/0352996 | A1* | 12/2016 | Qian ....................... | G06T 5/007 |

* cited by examiner

*Primary Examiner* — Hung H Lam (57) ABSTRACT

An imaging system includes an image sensing unit and a processing unit. The image sensing unit captures a plurality of images of an object, wherein each of the images includes a plurality of pixels. The processing unit obtains a plurality of sets of image data according to the images, wherein each set of image data includes a plurality of characteristic values. The processing unit calculates a plurality of difference parameters of the characteristic values of every two sets of image data. The processing unit accumulates the difference parameters within a predetermined time period to obtain a plurality of accumulated difference parameters corresponding to the pixels. The processing unit determines a plurality of weighting values corresponding to the pixels according to the accumulated difference parameters. The processing unit performs an image processing process according to the sets of image data and the weighting values.

20 Claims, 5 Drawing Sheets

IMAGING SYSTEM AND IMAGING METHOD

BACKGROUND OF THE INVENTION

1. Field of the Invention

The invention relates to an imaging system and an imaging method and, more particularly, to an imaging system and an imaging method capable of improving image processing accuracy effectively.

2. Description of the Prior Art

An intraoral scanner scans a tooth by projecting a light onto the tooth and then transmits the scanned image to a computer, so as to establish a tooth model. During the operation of the intraoral scanner, there may be dust, water stain, scratch, etc. on a reflecting mirror, a lens or other optical components, such that the scanned image may have a defect. If a user cannot perceive the defect in the scanned image in time, the follow-up image processing accuracy (e.g. establish a 3D model) will be affected.

SUMMARY OF THE INVENTION

An objective of the invention is to provide an imaging system and an imaging method capable of improving image processing accuracy effectively.

According to an embodiment of the invention, an imaging system comprises an image sensing unit and a processing unit, wherein the processing unit is electrically connected to the image sensing unit. The image sensing unit captures a plurality of images of an object, wherein each of the images comprises a plurality of pixels. The processing unit obtains a plurality of sets of image data according to the images, wherein each set of image data comprises a plurality of characteristic values. The processing unit calculates a plurality of difference parameters of the characteristic values of every two sets of image data. The processing unit accumulates the difference parameters within a predetermined time period to obtain a plurality of accumulated difference parameters corresponding to the pixels. The processing unit determines a plurality of weighting values corresponding to the pixels according to the accumulated difference parameters. The processing unit performs an image processing process according to the sets of image data and the weighting values.

According to another embodiment of the invention, an imaging method comprises steps of capturing a plurality of images of an object, wherein each of the images comprises a plurality of pixels; obtaining a plurality of sets of image data according to the images, wherein each set of image data comprises a plurality of characteristic values; calculating a plurality of difference parameters of the characteristic values of every two sets of image data; accumulating the difference parameters within a predetermined time period to obtain a plurality of accumulated difference parameters corresponding to the pixels; determining a plurality of weighting values corresponding to the pixels according to the accumulated difference parameters; and performing an image processing process according to the sets of image data and the weighting values.

As mentioned in the above, after capturing the images, the invention obtains the accumulated difference parameters of the pixels within a predetermined time period according to the characteristic values (e.g. gray level values of pixels or depth values of voxels) of the image data (e.g. pixel data or voxel data) and then determines the weighting values of the pixels according to the accumulated difference parameters. When the accumulated difference parameter is small, it means that the pixel is abnormal (e.g. there may be dust, water stain, scratch, etc. on the pixel). Accordingly, the invention may assign a small weighting value for the pixel. On the other hand, when the accumulated difference parameter is large, it means that the pixel is normal. Accordingly, the invention may assign a large weighting value for the pixel. Then, the invention performs the image processing process by the image data and the weighting values of the pixels (e.g. establish a 3D model, determine a position of the object, etc.). Therefore, the invention can prevent the image processing accuracy from being affected by abnormal pixel.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
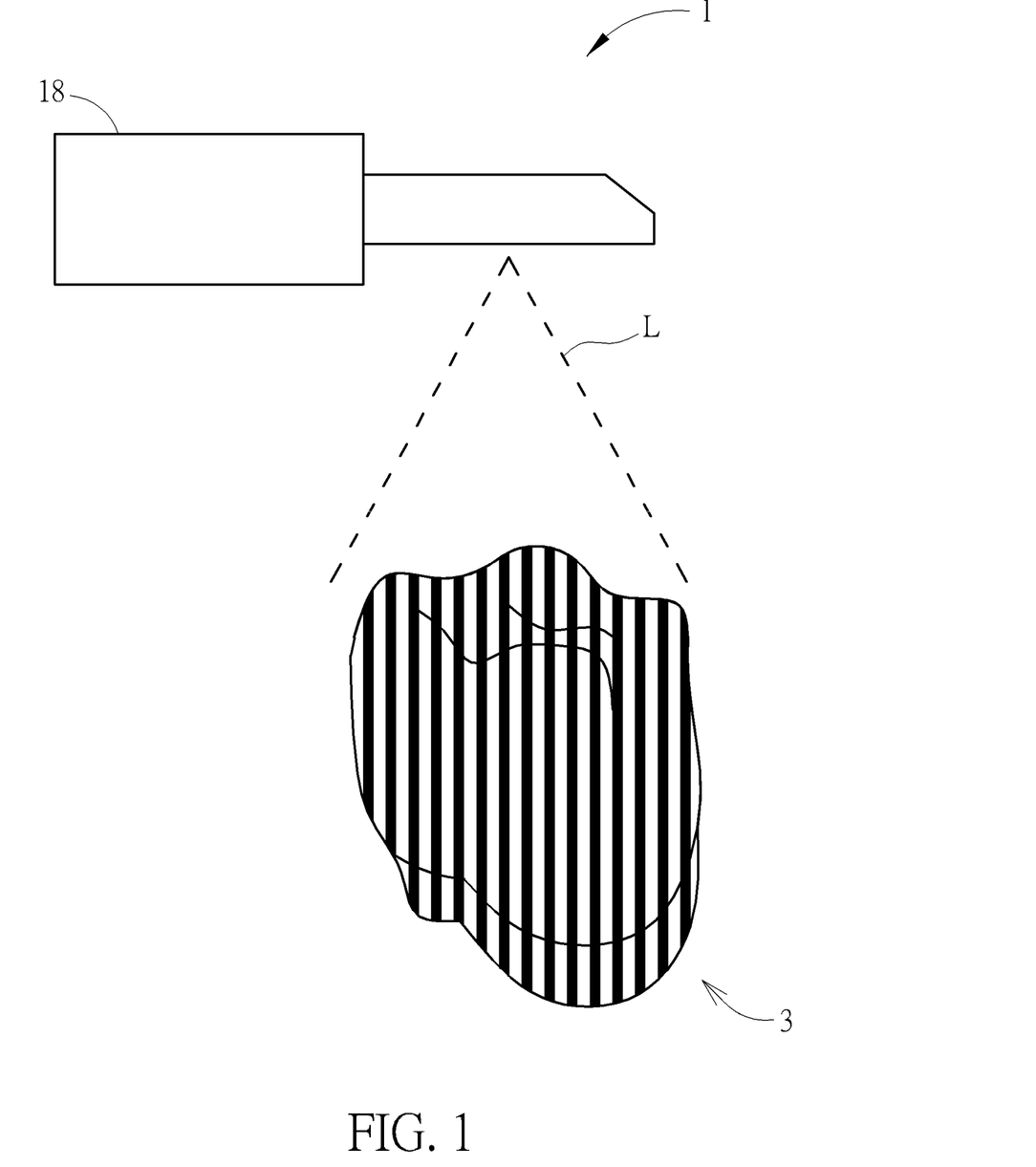
FIG. 1 is a schematic diagram illustrating that an imaging system is scanning an object according to an embodiment of the invention.
Figure 2:
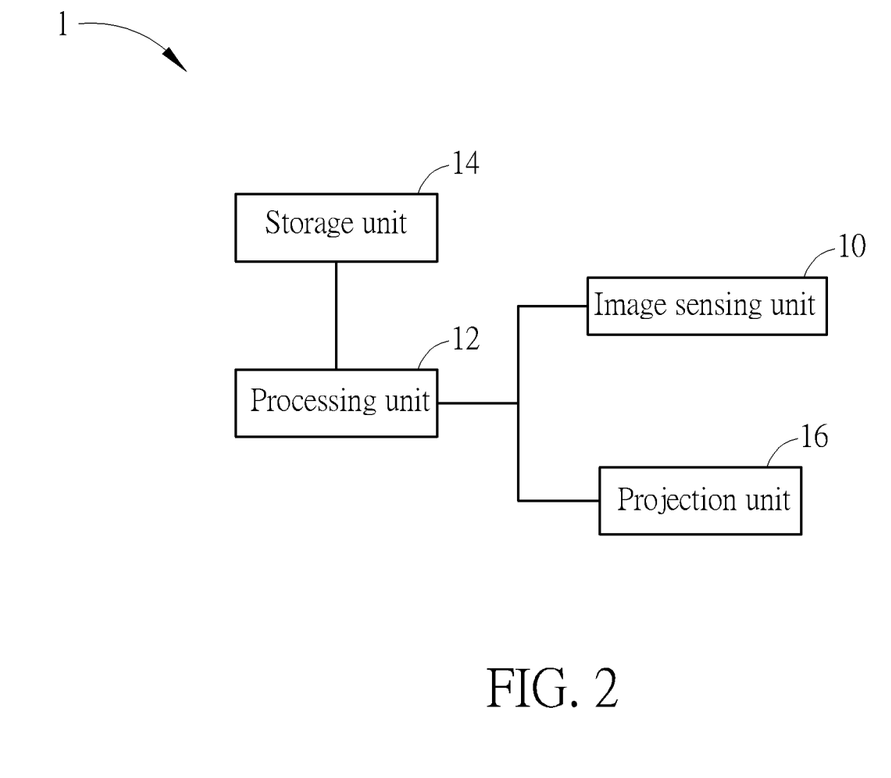
FIG. 2 is a functional block diagram illustrating the imaging system shown in FIG. 1.
Figure 3:
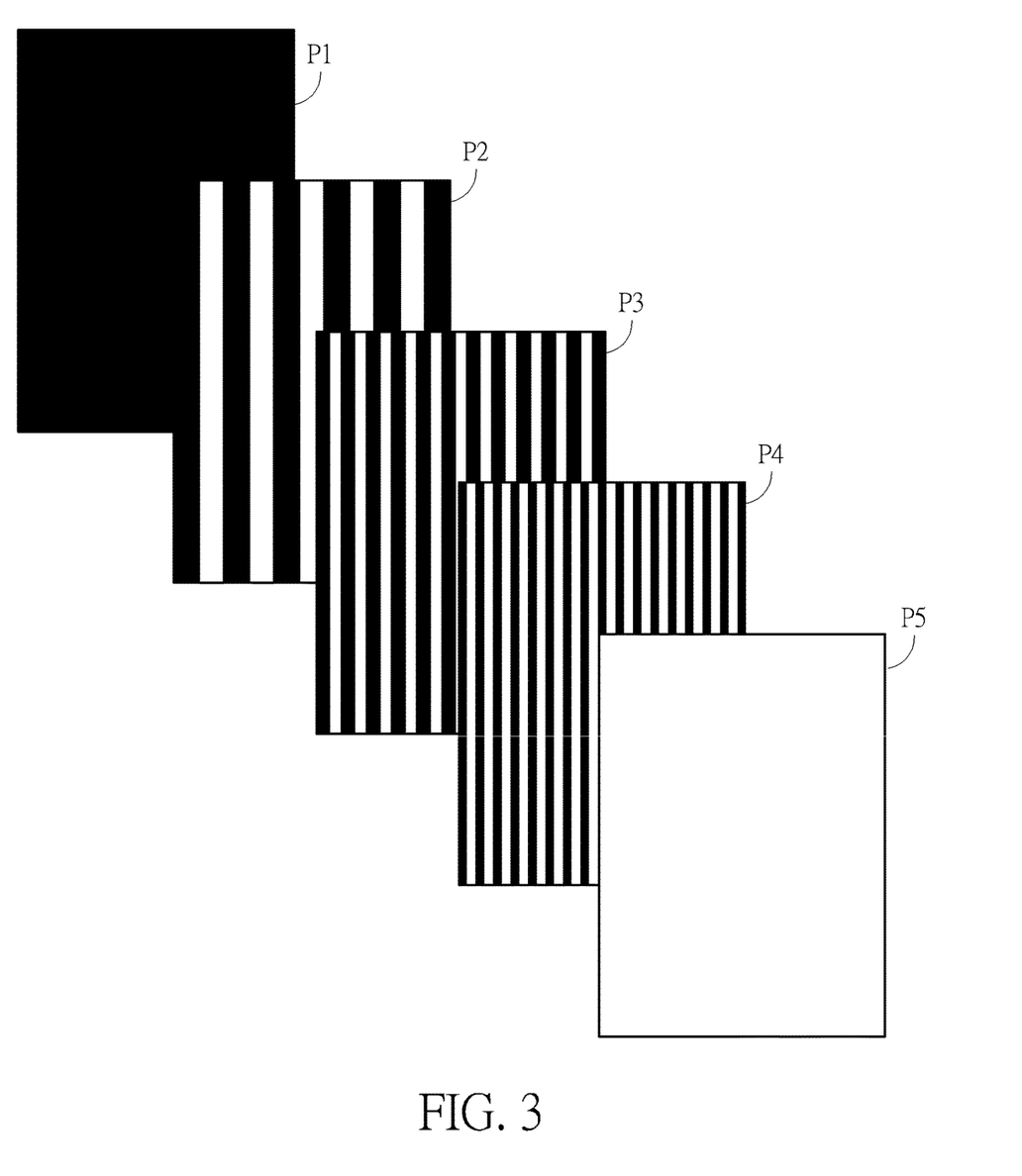
FIG. 3 is a schematic diagram illustrating a plurality of patterns stored in the storage unit shown in FIG. 2.
Figure 4:
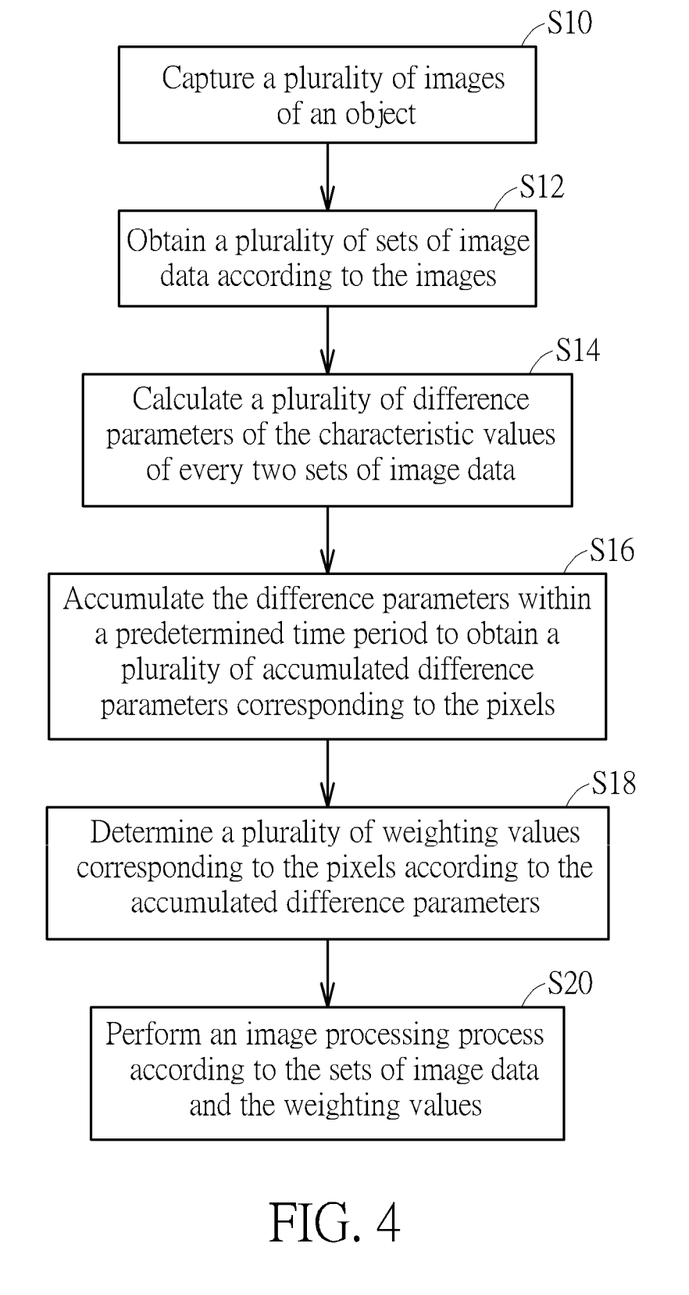
FIG. 4 is a flowchart illustrating an imaging method according to an embodiment of the invention.

Referring to FIGS. 1 to 4, FIG. 1 is a schematic diagram illustrating that an imaging system 1 is scanning an object 3 according to an embodiment of the invention, FIG. 2 is a functional block diagram illustrating the imaging system 1 shown in FIG. 1, FIG. 3 is a schematic diagram illustrating a plurality of patterns P1-P5 stored in the storage unit 14 shown in FIG. 2, and FIG. 4 is a flowchart illustrating an imaging method according to an embodiment of the invention. The imaging method shown in FIG. 4 is applied to the imaging system 1 shown in FIGS. 1 and 2. It should be noted that each part or function of the control logic of the imaging method of the invention may be implemented by software, hardware or the combination thereof.

As shown in FIG. 1, the imaging system 1 of the invention is used to scan an object 3, so as to establish a 3D model of the object 3. In this embodiment, the imaging system 1 may be, but not limited to, an intraoral scanner and the object 3 may be, but not limited to, a tooth. In another embodiment, the imaging system 1 may be a projection screen and the object 3 may be a projection plane. In another embodiment, the imaging system 1 may be a 3D model establishing device and the object 3 may be any object.

As shown in FIGS. 1 and 2, the imaging system 1 comprises an image sensing unit 10, a processing unit 12, a storage unit 14, a projection unit 16 and a casing 18, wherein the processing unit 12 is electrically connected to the image sensing unit 10, the storage unit 14 and the projection unit 16. In this embodiment, the image sensing unit 10, the processing unit 12, the storage unit 14 and the projection unit 16 may be disposed in the casing 18, so as to form an intraoral scanner. In practical applications, the image sensing unit 10 may be a charge-coupled device (CCD) sensor, a complementary metal-oxide semiconductor (CMOS) sensor or other sensors; the processing unit 12 may be a processor or a controller with data processing/calculating function; the storage unit 14 may be a memory or other data storage devices; and the projection unit 16 may be a digital light processing (DLP) module or other projection modules. In general, the imaging system 1 may be further equipped with some necessary hardware or software components for specific purposes, such as a circuit board, applications, a communication module, a power supply, etc., and it depends on practical applications.

In this embodiment, the storage unit 14 may store a plurality of patterns P1-P5, wherein the pattern P1 may be a black pattern, each of the patterns P2-P4 may comprise a plurality of black stripes and a plurality of white stripes, and the pattern P5 may be a white pattern, as shown in FIG. 3. The processing unit 12 may control the projection unit 16 to project the patterns P1-P5 onto the object 3 by a predetermined frequency and control the image sensing unit 10 to capture a plurality of images of the object 3 including the patterns P1-P5. Then, the processing unit 12 analyzes the images to establish a 3D model of the object 3 according to the variation of the patterns P1-P5.

As shown in FIG. 1, when the imaging system 1 is scanning the object 3, the projection unit 16 projects a light L onto the object 3, wherein the light L is a structured light comprising the patterns P1-P5. It should be noted that the light L may also be a structured light comprising one single pattern or other light according to practical applications. Then, the image sensing unit 10 captures a plurality of images of the object 3 (step S10 in FIG. 4), wherein each of the images comprises a plurality of pixels. For example, if the pixels of the image sensing unit 10 are 640*480, each of the images comprises 640*480 pixels.

Then, the processing unit 12 obtains a plurality of sets of image data according to the images (step S12 in FIG. 4), wherein each set of image data comprises a plurality of characteristic values. Then, the processing unit 12 calculates a plurality of difference parameters of the characteristic values of every two sets of image data (step S14 in FIG. 4). It should be noted that if the light L is a structured light comprising a plurality of patterns (e.g. the patterns P1-P5 shown in FIG. 3), the processing unit 12 calculates the difference parameters of the characteristic values of every two sets of image data corresponding to an identical pattern.

Then, the processing unit 12 accumulates the difference parameters within a predetermined time period (e.g. 3 seconds, 5 seconds, etc.) to obtain a plurality of accumulated difference parameters corresponding to the pixels (step S16 in FIG. 4). Then, the processing unit 12 determines a plurality of weighting values corresponding to the pixels according to the accumulated difference parameters (step S18 in FIG. 4). Then, the processing unit 12 performs an image processing process according to the sets of image data and the weighting values (step S20 in FIG. 4).

In this embodiment, the processing unit 12 may decode the images in the step S12 to obtain a plurality of sets of pixel data, wherein the aforesaid image data may be the pixel data, and the aforesaid characteristic value may be a gray level value of a pixel. In another embodiment, after obtaining the sets of pixel data, the processing unit 12 may further calculate a plurality of sets of voxel data in the step S12 according to the sets of pixel data, wherein the aforesaid image data may be the voxel data, and the aforesaid characteristic value may be a depth value of a voxel.

In the following, the invention takes the pixel data to be the image data and takes the gray level value of the pixel to be the characteristic value for illustration purpose. Referring to Tables 1 to 3, Tables 1 to 3 record the gray level values, the difference parameters and the accumulated difference parameters of the pixels X1, X2, X3 in the images I1-I6. In this embodiment, the aforesaid difference parameter may be one of a difference value and a number of difference times of the characteristic values of every two sets of image data.

TABLE 1

| Image | I1 | I2 | I3 | I4 | I5 | I6 |
|---|---|---|---|---|---|---|
| Gray level value (characteristic value) of pixel X1 | 40 | 23 | 32 | 156 | 150 | 203 |
| Difference of gray level value (difference parameter) | NA NA | $|I_2 - I_1|$ 17 | $|I_3 - I_2|$ 9 | $|I_4 - I_3|$ 124 | $|I_5 - I_4|$ 6 | $|I_6 - I_5|$ 53 |
| Number of difference times (difference parameter) | NA | 1 | If the difference of gray level value is larger than a threshold (e.g. 4), count one time for the number of difference times. 1 | 1 | 1 | 1 |
| Accumulated difference parameter (difference value: sum of difference of gray level value) | | | 209 | | | |
| Accumulated difference parameter (difference value: average of difference of gray level value) | | | 41.8 | | | |
| Accumulated difference parameter (number of difference times) | | | 5 | | | |

TABLE 2

| Image | I1 | I2 | I3 | I4 | I5 | I6 |
|---|---|---|---|---|---|---|
| Gray level value (characteristic value) of pixel X2 | 121 | 122 | 127 | 123 | 123 | 120 |
| Difference of gray level value (difference parameter) | NA NA | $|I_2 - I_1|$ 1 | $|I_3 - I_2|$ 5 | $|I_4 - I_3|$ 4 | $|I_5 - I_4|$ 0 | $|I_6 - I_5|$ 3 |
| Number of difference times (difference parameter) | NA | 0 | If the difference of gray level value is larger than a threshold (e.g. 4), count one time for the number of difference times. 1 | 0 | 0 | 0 |
| Accumulated difference parameter (difference value: sum of difference of gray level value) | | | 13 | | | |
| Accumulated difference parameter | | | 2.6 | | | |

TABLE 2-continued

| Image | I1 | I2 | I3 | I4 | I5 | I6 |
|---|---|---|---|---|---|---|
| parameter (difference value: average of difference of gray level value) | | | | | | |
| Accumulated difference parameter (number of difference times) | | | | 1 | | |

TABLE 3

| Image | I1 | I2 | I3 | I4 | I5 | I6 |
|---|---|---|---|---|---|---|
| Gray level value (characteristic value) of pixel X3 | 56 | 56 | 56 | 57 | 56 | 56 |
| Difference of gray level value (difference parameter) | NA NA | $\|I_2 - I_1\|$ 0 | $\|I_3 - I_2\|$ 0 | $\|I_4 - I_3\|$ 1 | $\|I_5 - I_4\|$ 1 | $\|I_6 - I_5\|$ 0 |
| Number of difference times (difference parameter) | NA | If the difference of gray level value is larger than a threshold (e.g. 4), count one time for the number of difference times. | | | | |
| | NA | 0 | 0 | 0 | 0 | 0 |
| Accumulated difference parameter (difference value: sum of difference of gray level value) | | | 2 | | | |
| Accumulated difference parameter (difference value: average of difference of gray level value) | | | 0.4 | | | |
| Accumulated difference parameter (number of difference times) | | | 0 | | | |

In this embodiment, the storage unit 14 may store a predetermined relation between a plurality of accumulated difference thresholds and the weighting values. Accordingly, in the step S18, the processing unit 12 may determine the weighting values corresponding to the pixels according to the accumulated difference parameters and the predetermined relation. Referring to Tables 4 to 6, Tables 4 to 6 record different predetermined relations corresponding to different accumulated difference parameters. The invention may be implemented by one of the predetermined relations recorded in Tables 4 to 6 selectively.

TABLE 4

| | Accumulated difference parameter D (difference value: sum of difference of gray level value) | | | | |
|---|---|---|---|---|---|
| Accumulated difference threshold | 0 | $0 < D \leq 5$ | $5 < D \leq 15$ | $15 < D \leq 25$ | $D \geq 25$ |
| Weighting value | 0 | 0.05 | 0.15 | 0.25 | 1.00 |

TABLE 5

| | Accumulated difference parameter D (difference value: average of difference of gray level value) | | | | |
|---|---|---|---|---|---|
| Accumulated difference threshold | 0 | $0 < D \leq 1$ | $1 < D \leq 3$ | $3 < D \leq 5$ | $D \geq 5$ |
| Weighting value | 0 | 0.05 | 0.15 | 0.25 | 1.00 |

TABLE 6

| | Accumulated difference parameter (number of difference times) | | | |
|---|---|---|---|---|
| Accumulated difference threshold | 0 | 1-3 | 4 | 5 |
| Weighting value | 0.00 | 0.15 | 0.25 | 1.00 |

Therefore, according to Tables 1-6, the weighting values of the pixels X1-X3 may be represented by Tables 7-9.

TABLE 7

| Pixel X1 | | |
|---|---|---|
| Accumulated difference parameter D (difference value: sum of difference of gray level value) | 209 | Look up Table 4, the weighting value is 1.00. |
| Accumulated difference parameter D (difference value: average of difference of gray level value) | 41.8 | Look up Table 5, the weighting value is 1.00. |
| Accumulated difference parameter (number of difference times) | 5 | Look up Table 6, the weighting value is 1.00. |

TABLE 8

| Pixel X2 | | |
|---|---|---|
| Accumulated difference parameter D (difference value: sum of difference of gray level value) | 13 | Look up Table 4, the weighting value is 0.15. |
| Accumulated difference parameter D (difference value: average of difference of gray level value) | 2.6 | Look up Table 5, the weighting value is 0.15. |

TABLE 8-continued

Pixel X2

| | | |
|---|---|---|
| Accumulated difference parameter (number of difference times) | 1 | Look up Table 6, the weighting value is 0.15. |

TABLE 9

Pixel X3

| | | |
|---|---|---|
| Accumulated difference parameter D (difference value: sum of difference of gray level value) | 2 | Look up Table 4, the weighting value is 0.05. |
| Accumulated difference parameter D (difference value: average of difference of gray level value) | 0.4 | Look up Table 5, the weighting value is 0.05. |
| Accumulated difference parameter (number of difference times) | 0 | Look up Table 6, the weighting value is 0.00. |

When the accumulated difference parameter is small, it means that the pixel is abnormal (e.g. there may be dust, water stain, scratch, etc. on the pixel). Accordingly, the invention may assign a small weighting value for the pixel. On the other hand, when the accumulated difference parameter is large, it means that the pixel is normal. Accordingly, the invention may assign a large weighting value for the pixel. After determining the weighting value corresponding to each pixel by the aforesaid manner, the processing unit 12 may perform an image processing process according to the image data and the weighting values of the pixels. Therefore, the invention can prevent the image processing accuracy from being affected by abnormal pixel.

It should be noted that when the image data is voxel data and the characteristic value is a depth value of a voxel, the embodiment of the voxel is similar to the aforesaid embodiment of the pixel, so it will not be depicted herein again.

In this embodiment, the invention may store a weighting table in the storage unit 14, wherein the weighting table may record a plurality of weighting values of the pixels in advance. Accordingly, after determining the weighting value corresponding to each pixel by the aforesaid manner, the processing unit 12 may further update the weighting table for next image processing process.

In this embodiment, the image processing process may be performed to establish a 3D model of the object 3. For example, if the invention is applied to an intraoral scanner, the 3D model of the object 3 is a 3D model of a tooth. In another embodiment, if the invention is applied to a projection screen, the image processing process may be performed to determine a position of the object 3 in the images, so as to recognize a real position of the object 3 with respect to the projection screen.

Figure 5:
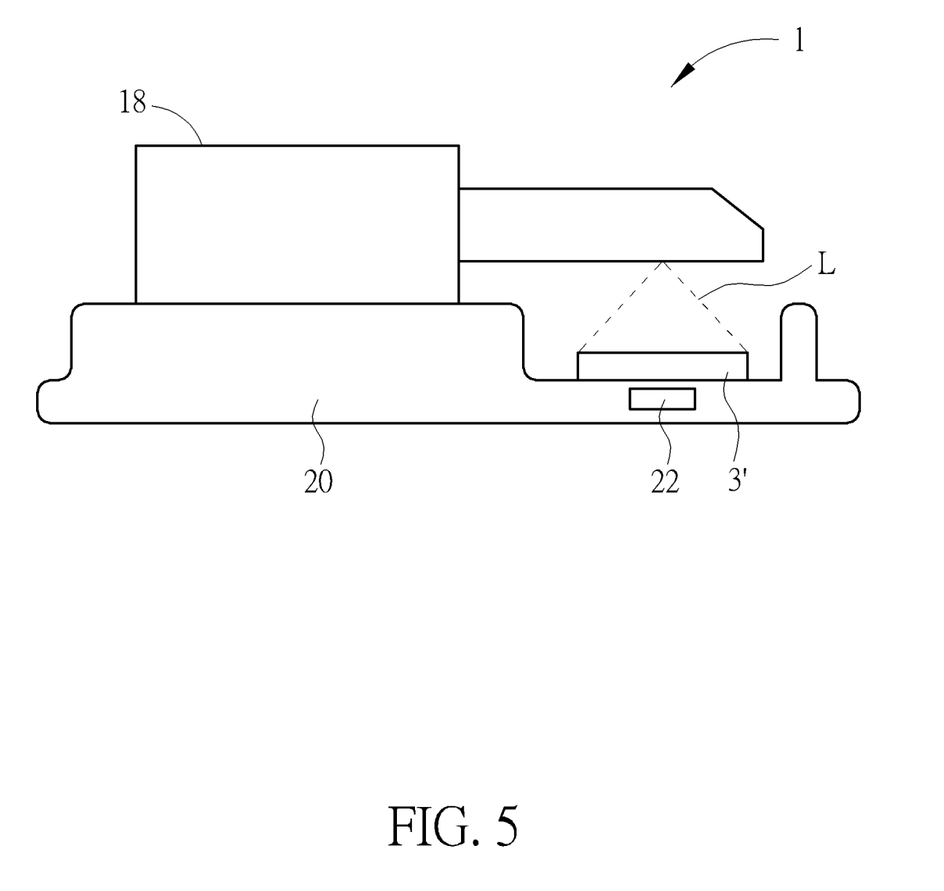
FIG. 5 is a schematic diagram illustrating the casing of the imaging system shown in FIG. 1 being placed on a support base.

Referring to FIG. 5, FIG. 5 is a schematic diagram illustrating the casing 18 of the imaging system 1 shown in FIG. 1 being placed on a support base 20. As shown in FIG. 5, the imaging system 1 may further comprise a support base 20. In this embodiment, an object 3' may be disposed on the support base 20. Furthermore, the support base 20 may comprise a driving unit 22, wherein the processing unit 12 is electrically connected to the driving unit 22. When the imaging system 1 is idle, a user may place the casing 18 on the support base 20, such that the image sensing unit 10 captures a plurality of images of the object 3'. When the image sensing unit 10 captures the images of the object 3', the processing unit 12 controls the driving unit 22 to selectively drive one of the casing 18 and the object 3' to move, such that the images captured by the image sensing unit 10 generate variation. Then, the processing unit 12 may perform the steps S12-S18 shown in FIG. 5 to determine the weighting value corresponding to each pixel. If the storage unit 14 stores a weighting table, the processing unit 12 may further update the weighting table for next image processing process.

In this embodiment, the object 3' may be a rolling belt or a rotating plate and the driving unit 22 may be a motor. The motor may be connected to the rolling belt or the rotating plate, so as to drive the rolling belt or the rotating plate to move. In another embodiment, the driving unit 22 may be a movable mechanism. When the casing 18 is placed on the movable mechanism, the movable mechanism may drive the casing 18 to move.

In another embodiment, the image sensing unit 10 and the projection unit 16 may be disposed in the casing 18 to form an intraoral scanner, and the processing unit 12 and the storage unit 14 may be disposed in a host device (e.g. computer). The intraoral scanner and the computer may communicate with each other by wired or wireless manner to transmit signals. At this time, the patterns P1-P5 shown in FIG. 3 are stored in the intraoral scanner.

As mentioned in the above, after capturing the images, the invention obtains the accumulated difference parameters of the pixels within a predetermined time period according to the characteristic values (e.g. gray level values of pixels or depth values of voxels) of the image data (e.g. pixel data or voxel data) and then determines the weighting values of the pixels according to the accumulated difference parameters. When the accumulated difference parameter is small, it means that the pixel is abnormal (e.g. there may be dust, water stain, scratch, etc. on the pixel). Accordingly, the invention may assign a small weighting value for the pixel. On the other hand, when the accumulated difference parameter is large, it means that the pixel is normal. Accordingly, the invention may assign a large weighting value for the pixel. Then, the invention performs the image processing process by the image data and the weighting values of the pixels (e.g. establish a 3D model, determine a position of the object, etc.). Therefore, the invention can prevent the image processing accuracy from being affected by abnormal pixel.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. An imaging system comprising:
    an image sensing unit capturing a plurality of images of an object, each of the images comprising a plurality of pixels; and
    a processing unit electrically connected to the image sensing unit, the processing unit obtaining a plurality of sets of image data according to the images, each set of image data comprising a plurality of characteristic values, the processing unit calculating a plurality of difference parameters of the characteristic values of every two sets of image data, the processing unit accumulating the difference parameters within a predetermined time period to obtain a plurality of accumulated difference parameters corresponding to the pixels, the processing unit determining a plurality of weighting values corresponding to the pixels according to the accumulated difference parameters, the processing unit performing an image processing process according to the sets of image data and the weighting values.

2. The imaging system of claim 1, further comprising a storage unit, the processing unit being electrically connected to the storage unit, wherein the storage unit stores a predetermined relation between a plurality of accumulated difference thresholds and the weighting values, and the processing unit determines the weighting values corresponding to the pixels according to the accumulated difference parameters and the predetermined relation.

3. The imaging system of claim 1, wherein the difference parameter may be one of a difference value and a number of difference times of the characteristic values of every two sets of image data.

4. The imaging system of claim 1, wherein the processing unit decodes the images to obtain a plurality of sets of pixel data, the image data is the pixel data, and the characteristic value is a gray level value of a pixel.

5. The imaging system of claim 1, wherein the processing unit decodes the images to obtain a plurality of sets of pixel data, the processing unit calculates a plurality of sets of voxel data according to the sets of pixel data, the image data is the voxel data, and the characteristic value is a depth value of a voxel.

6. The imaging system of claim 1, further comprising a projection unit projecting a light onto the object, the processing unit being electrically connected to the projection unit, the light being a structured light comprising at least one pattern.

7. The imaging system of claim 6, wherein the processing unit calculates the difference parameters of the characteristic values of every two sets of image data corresponding to an identical pattern.

8. The imaging system of claim 1, wherein the image processing process is performed to establish a 3D model of the object.

9. The imaging system of claim 1, wherein the image processing process is performed to determine a position of the object in the images.

10. The imaging system of claim 1, further comprising a casing and a support base, the image sensing unit, the storage unit and the processing unit being disposed in the casing, the casing being placed on the support base, the object being disposed on the support base, the support base comprising a driving unit, the processing unit being electrically connected to the driving unit, wherein when the image sensing unit captures the images of the object, the processing unit controls the driving unit to selectively drive one of the casing and the object to move.

11. An imaging method comprising steps of:
capturing a plurality of images of an object, wherein each of the images comprises a plurality of pixels;
obtaining a plurality of sets of image data according to the images, wherein each set of image data comprises a plurality of characteristic values;
calculating a plurality of difference parameters of the characteristic values of every two sets of image data;
accumulating the difference parameters within a predetermined time period to obtain a plurality of accumulated difference parameters corresponding to the pixels;
determining a plurality of weighting values corresponding to the pixels according to the accumulated difference parameters; and
performing an image processing process according to the sets of image data and the weighting values.

12. The imaging method of claim 11, further comprising step of:
setting a predetermined relation between a plurality of accumulated difference thresholds and the weighting values;
wherein the imaging method determines the weighting values corresponding to the pixels according to the accumulated difference parameters and the predetermined relation.

13. The imaging method of claim 11, wherein the difference parameter may be one of a difference value and a number of difference times of the characteristic values of every two sets of image data.

14. The imaging method of claim 11, wherein the imaging method decodes the images to obtain a plurality of sets of pixel data, the image data is the pixel data, and the characteristic value is a gray level value of a pixel.

15. The imaging method of claim 11, wherein the imaging method decodes the images to obtain a plurality of sets of pixel data, the imaging method calculates a plurality of sets of voxel data according to the sets of pixel data, the image data is the voxel data, and the characteristic value is a depth value of a voxel.

16. The imaging method of claim 11, further comprising step of:
before capturing the images, projecting a light onto the object, wherein the light is a structured light comprising at least one pattern.

17. The imaging method of claim 16, wherein the imaging method calculates the difference parameters of the characteristic values of every two sets of image data corresponding to an identical pattern.

18. The imaging method of claim 11, wherein the image processing process is performed to establish a 3D model of the object.

19. The imaging method of claim 11, wherein the image processing process is performed to determine a position of the object in the images.

20. The imaging method of claim 11, wherein the imaging method captures the images of the object by an image sensing unit and the imaging method further comprises step of:
when the image sensing unit captures the images of the object, selectively drive one of the image sensing unit and the object to move.

* * * * *